United States Patent [19]

Verdini et al.

[11] Patent Number: 4,638,046
[45] Date of Patent: Jan. 20, 1987

[54] RETRO-INVERSO C-TERMINAL HEXAPEPTIDE ANALOGUES OF SUBSTANCE P

[75] Inventors: Antonio S. Verdini; Giuseppe C. Viscomi, both of Rome, Italy

[73] Assignee: ENI-Ente Nazionale Idrocarburi, Rome, Italy

[21] Appl. No.: 689,911

[22] Filed: Jan. 9, 1985

[30] Foreign Application Priority Data

Jan. 13, 1984 [IT] Italy ............................... 19142 A/84

[51] Int. Cl.$^4$ ............................................. C07K 7/02
[52] U.S. Cl. ..................................... 530/332; 530/329
[58] Field of Search ................ 260/112.5 R; 530/332, 530/329

[56] References Cited

U.S. PATENT DOCUMENTS 3,862,114 1/1975 Scandrett .................... 260/112.5 R
4,439,360 3/1984 Verdini et al. ............... 260/112.5 R
4,472,305 9/1984 Hansen et al. ............... 260/112.5 R
4,481,139 11/1984 Folkers et al. ............... 260/112.5 R
4,485,099 11/1984 Boger et al. ................. 260/112.5 R

*Primary Examiner*—Delbert R. Phillips
*Attorney, Agent, or Firm*—Hedman, Gibson, Costigan & Hoare

[57] ABSTRACT

New retro-inverso peptides and peptide derivatives in the form of analogues of C-terminal hexapeptide fragments of Substance P, which are pharmacologically active, possess prolonged action with time, and are of general formula (I):

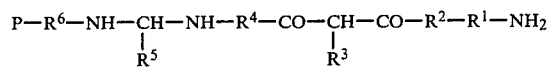

they being useful as vasedilators.

15 Claims, No Drawings

RETRO-INVERSO C-TERMINAL HEXAPEPTIDE ANALOGUES OF SUBSTANCE P

This invention relates to new peptides and peptide derivatives in the form of analogues of C-terminal hexapeptide fragments of Substance P, which are pharmacologically active and useful as vasodilators. Substance P, an undecapeptide of Arg-Pro-Lys-Pro-Gln-Gln-Phe-Phe-Gly-Leu-Met-NH2 sequence, which is considered to be a neuromodulator and neurotransmitter of the central nervous system, is probably involved both in the neurotransmission of pain sensations and in the sensory axonal reflexes [Celander O, et al, Acta Physiol. Scand. 29, 359 (1953); Haensler G. et al., Naunyn-Schiemedeberg's Arch. Pharmacol., 314, 111 (1980)].

In addition it is one of the most powerful of known vasodilators, possessing the property in the peripheral nervous system of contracting the smooth muscle. [Henbeck F. et al., Int. Rev. Neurobiol., 4, 159 (1962); Chernuk A. M. et al., Exp. Biol. Med. 90, 1165 (1980); Schrauwen E. et al., Phlungers Arch. Eur. J. Physio. 986, 281 (1980)]. It is known that the various activities of Substance P are also preserved in its C-terminal segments, in particular in the C-terminal hexa, hepta and octapeptide fragments.

In this respect, structure-function studies carried out on a series of partial sequences and fragments of Substance P, prepared by chemical synthesis, have shown that the Substance P receptor interacts best with the natural C-terminal hexa and heptapeptide sequences, and that extending the chain beyond the C-terminal heptapeptide produces effects of negligible importance.

However, both Substance P and its C-terminal hexa, hepta and octapeptide fragments are rapidly degraded by numerous proteolytic enzymes.

In particular, a highly specific membrane enzyme isolated from the brain hydrolyses three different Substance P bonds, namely Gln6-Phe7, Phe7-Phe8 and Phe8-Gly9 [Hec G. M. et al., Eur. J. Biochem. 114, 315 (1981)].

The extreme lability of Substance P and its C-terminal fragments towards enzymes makes their use in pharmacology of little advantage and problematical.

Attempts have been made to stabilise the molecule by using the methods described in Biochem. Biophys. Res. Comm. 90. 347 (1979) and in Eur. J. Biochem. 114 329, (1981) respectively. However, in the case of Substance P, a loss of power of the molecule has been observed.

It has now been found that by applying the criterion of retro-inversion of suitable peptide bonds to the C-terminal hexapeptide fragments of Substance P, it is possible to obtain metabolically stable peptides with unaltered biological activity.

The present invention relates to new peptides and peptide derivatives in the form of analogues of the hexapeptide fragments of Substance P in which two of the peptide bonds which have proved to be most susceptible to endopeptidase action have been simultaneously inverted. In particular we have retro-inverted the Phe7-Phe8 and Phe8-Gly9 bonds of the sequence of the C-terminal hexapeptide fragment of Substance P.

The inversion of two adjacent peptide bonds involves the simultaneous transformation of the three amino acids of the retro-inverted peptide segment. In order to maintain the biological activity of said peptide unaltered, it is necessary to effect the inversion in such a manner that the three-dimensional orientation of the peptide side-chains is maintained.

The amino acid residue closest to the N-terminus is transformed into a derivative of gem-diaminoalkylmethane type, that closest to the C-terminus is transformed into a malonyl or 2-substituted malonyl derivative, and the amino acid residue between the two retro-inverted bonds possesses D configuration.

The malonyl or 2-substituted malonyl residue is incorporated into the peptide chain as described by Goodman M. in "Perspectives in Peptide Chemistry", A. Eberle, R. Geiger and T. Wieland, Editors, Karger, Basel 1980 p. 283, whereas the gem-diaminoalkylmethane derivative is introduced as described in Italian Pat. Appln. No. 25755A/81 filed on Dec. 22, 1981.

The retro-inverse peptides according to the present invention are those corresponding to general formula (I):

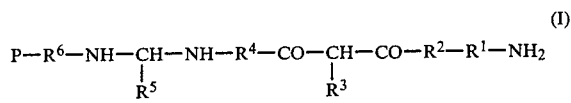

in which P is a hydrogen atom, a linear or branched aliphatic alkyl group with 1-6 carbon atoms, or a saturated or unsaturated linear or branched chain aliphatic acyl group such as formyl, acetyl, propionyl, n-butyryl, isobutyryl, n-valeryl, isovaleryl, hexanoyl, isohexanoyl, heptanoyl, octanoyl, crotonoyl, methacryloyl, acryloyl; or a substituted acyl group such as hydroxyacetyl, 2-hydroxypropionyl, 3-hydroxypropionyl, aminoacetyl, 4-hydroxyphenylacetyl, 4-hydroxyphenylpropionyl, 2-aminopropionyl, 3-aminopropionyl, O-ethyl-malonyl, ethoxyformyl, methoxyformyl, 3-methoxypropionyl, 3-ethoxypropionyl, chloroacetyl, dichloroacetyl, 2-chloropropionyl, 3-chloropropionyl, 2,3-dichloropropionyl, bromoacetyl, 4-hydroxy-3,5-diiodophenylacetyl, 3-oxobutyryl, 3-oxovaleryl, 4-oxovaleryl, methylthioacetyl, 3-methylthiopropionyl, ethylthioacetyl, 3-ethylthiopropionyl, nicotinoyl, 4-aminobutyryl, $N^\alpha$-[(1-(9-adenyl)$\beta$-D-ribofuranuronosyl], $N^\alpha$-[(1-(9-hypoxanthyl)-$\beta$-D-ribofuranuronosyl]; or a group such as benzyloxycarbonyl, tert-butyloxycarbonyl, tert-amyloxycarbonyl, isobornyloxycarbonyl, adamantyloxycarbonyl, or chloro or nitro-substituted benzyloxycarbonyl;

$R^1$ is a residue of methionine, methioninesulphoxide, methionine sulphone, selenomethionine, leucine, norleucine, valine or norvaline;

$R^2$ is a residue of leucine, norleucine, valine, norvaline, alanine or isoleucine;

$R^3$ is a hydrogen atom or methyl;

$R^4$ is an amino acid residue of D configuration such as phenylalanine, tryptophan, tyrosine, valine, norvaline, leucine, norleucine, isoleucine, serine or derivatives, threonine or derivatives, histadine or derivatives, methionine, methionine-S-methyl, methionine sulphone, arginine or derivatives, lysine or derivatives, ornithine or derivatives, 2,4-diaminobutyric acid or derivatives, 2,3-diaminopropionic acid or derivatives, glutamic acid or aspartic acid or their suitable derivatives;

$R^5$ is a hydrogen atom or the side-chain of amino acids such as phenylalanine, tyrosine, 4-chlorophenylalanine, O-benzyltyrosine (or their acetyl, cyclopentyl, tert-butyl-oxycarbonyl or 4-hydroxyphenylacetyl derivatives);

$R^6$ is an amino acid residue such as glutamine or derivatives, pyroglutamic acid, alanine, tyrosine, lysine or derivatives, proline, N-formyl-proline, β-alanine, N-acetyl-β-alanine, glycine, desaminophenylalanine, desaminoaspartic acid, methyldesaminoaspartic acid, or glutamic acid esters represented by general formula (II):

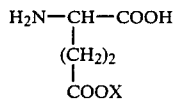

in which X is methyl, ethyl, methoxyethyl, methoxy(ethoxy)$_n$ethyl where n=1, 2 or 3.

Unless otherwise specified, each amino acid is of L form. A hexapeptide derivative of general formula (I) is synthesised by condensation, induced generally by DCC+HOBt, of a N,N'-diacylated gem-diaminoalkylmethane residue of general formula (III):

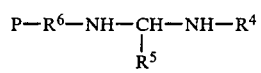

in which P, $R^6$, $R^5$ and $R^4$ have the aforesaid meanings and in which the amino, hydroxyl, carboxyl, carboxyamido, indole, imidazole, guanidino and mercaptide functions are suitably protected if present in P, $R^6$, $R^5$ or $R^4$, with a peptide fragment of general formula IV:

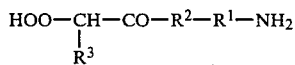

where $R^1$, $R^2$ and $R^3$ have the aforesaid meanings.

The synthesis of the diacylated gem-diaminoalkylmethane residue of general formula III and of the peptide fragment of general formula IV is conducted by known methods.

The identity of the products obtained is demonstrated by nuclear magnetic resonance spectroscopic analysis.

Product purity is demonstrated by reverse phase high pressure chromatography analysis (RP-hplc) using 0.01M ammonium acetate/MeCN as the eluent system, or thin layer chromatography analysis in silica gel using the following eluent systems: n-butanol/acetic acid/water (4:1:1); chloroform/methanol/acetic acid (85:10:5).

The following abbreviations are used in the synthesis descriptions: Boc=tert-butyloxycarbonyl; Z=benzyloxycarbonyl; MeO=methyl ester; MeOH=methyl alcohol; EtOH=ethyl alcohol; THF=tetrahydrofuran; EtAc=ethyl acetate; Et$_2$O=ethyl ether; MeCN=acetonitrile; DMF=N,N-dimethylformamide; DCC=N,N'-dicyclohexylcarbodiimide; DCU=N,N'-dicyclohexylurea; HOBt=N-hydroxybenzotriazole; TIB=1,1-bis(trifluoroacetoxy)iodobenzene; NMM=methylmorphaline; gPhe=

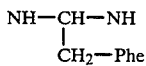

mGly=CO—CH$_2$—CO; mAla=

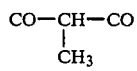

The pharmacological activity of the retro-inverse analogues of the present invention was verified by measuring the contraction of the isolated ileum of the guinea pig, as described by Rossel et al. in "Substance P" V. S. von Euler and B. Pernow Editors, Raven Press, New York 1977 p. 83, and by the in vivo evaluation of the main hemodynamic parameters.

It was found that the in vitro activity of said analogues is about 50 times less than that of Substance P.

In contrast, in vivo they demonstrate the same type of action as Substance P, ie a gradual hypotensive action prolonged with time, and a reduction in carotid arterial flow.

The subject matter and object of the invention will be more apparent from a reading of the following example, which is given only for illustrative purposes and must in no way be considered as limitative of the invention itself.

EXAMPLE

Synthesis of tert-butyloxycarbonyl-alanyl-gemphenylalanyl-D-phenylalanyl-malonyl-leucyl-methionineamide:

Synthesis of tert-butyloxycarbonyl-leucylmethionine methyl ester Boc-Leu-Met-OMe 1.0 equivalent of Boc-Leu is dissolved in anhydrous THF, and 1.0 equivalent of NMM and 1.1 equivalents of isobutyl chloroformate are added to the solution, which is cooled to −15° C. and maintained in a nitrogen atmosphere.

After two minutes, a solution prepared by dissolving 1.0 equivalent of HCl.Met-OMe and 1.0 equivalent of NMM in DMF is added. During the additions, the temperature is checked to ensure that it does not exceed −10° C. Having verified the disappearance of HCl.Met-OMe, the reaction is blocked by evaporating the mixture to dryness, the residue is taken up in EtAc and washed with a 5% bicarbonate solution, water, a 5% citric acid solution, and water.

The EtAc solution is then dried over magnesium sulphate, and the product is obtained by crystallisation, by suitably adding 30°–50° C. petroleum ether.

M.P.=102°–104° C.

$[\alpha]_{22}{}^{589} = -36.1°$ (C=1.0 in DMF)

Elementary analysis for C$_{17}$H$_{32}$N$_2$O$_5$S: Theoretical: C 54.23; H 8.57; N 7.44. Found: C 54.10; H 8.49; N 7.39.

Chromatography analysis (tlc and hplc) shows no presence of impurities, and the $^1$H n.m.r. spectrum confirms the molecular structure.

Synthesis of tert-butyloxycarbonyl-leucylmethionineamide Boc-Leu-Met-NH$_2$ 1.0 equivalent of Boc-Leu-Met-OMe is dissolved in anhydrous MeOH, and anhydrous ammonia is passed for 30 minutes into this solution, cooled to −5° C.

The solution, contained in a hermetically sealed vessel, is kept overnight at ambient temperature, after which the product is obtained in crystalline form by adding a volume of water equal to about 30% of the volume of MeOH.

M.P.=158°–160° C.

$[\alpha]_{22}{}^{589} = -35.4°$ (C=1.0 in DMF).

Elementary analysis for C$_{16}$H$_{31}$N$_3$O$_4$S: Theoretical: C 53.16; H 7.33; N 11.63; Found: C 53.03; H 7.23; N 11.50.

Chromatography analysis (tlc and hplc) shows no presence of impurities, and the $^1$H n.m.r. spectrum confirms the molecular structure.

Synthesis of malonylleucylmethionineamide methyl ester MeO-mGly-Leu-Met-NH$_2$ 1.0 equivalent of methyl monomalonate is dissolved in CH$_2$Cl$_2$, and 1.5 equivalents of HObt dissolved in DMF and 1.1. equivalents of DCC dissolved in CH$_2$Cl$_2$ are added to the solution cooled to 0° C. After 20 minutes, 1.0 equivalent of HCl.Leu-Met-NH$_2$ (obtained by removing the tert-butyloxycarbonyl from Boc-Leu-Met-NH$_2$ using 4.5N HCl in EtAc) is added to the cold mixture, followed by 1.1 equivalents of NMM. The ice bath is removed after about one hour, and having checked the disappearance of the hydrochloride, the reaction mixture is filtered, the precipitated dicyclohexylurea is washed with portions of THF, and the resultant solution and wash liquors are evaporated to dryness. The residue obtained is washed with small volumes of 5% sodium bicarbonate, water, 5% citric acid and water, and is then dried over P$_2$O$_5$.

The product is crystallised from DMF/Et$_2$O.

M.P.=184°–185° C.

$[\alpha]_{22}\cdot^{589} = -33.6$ (C=0.87 in DMF)

Elementary analysis for C$_{15}$H$_{27}$N$_3$O$_5$S: Theoretical: C 49.86; H 7.48; N 11.66; Found: C 49.75; H 7.43; N 11.60.

Chromatography analysis (tlc and hplc) shows no presence of impurities, and the $^1$H n.m.r. spectrum confirms the molecular structure.

Synthesis of malonylleucylmethionineamide HO-mGly-Leu-Met-NH$_2$ 1.0 equivalent of MeO-mGly-Leu-Met-NH$_2$ is dissolved in MeOH, and 3 equivalents of a 3M aqueous solution of NaOH are added to the solution.

Having verified the disappearance of the starting ester, the methanol is diluted with water, then eliminated, and the residual solution acidified to pH 2 with concentrated HCl, and extracted repeatedly with EtAc. The extracts are pooled, dried with magnesium sulphate and evaporated to dryness. The product is crystallised from dioxane/30°–50° C. petroleum ether.

M.P.=136°–138° C. (dec.)

$[\alpha]_{22}\cdot^{589} = -38.9$ (C=1.3 in DMF)

Elementary analysis for C$_{14}$H$_{25}$N$_3$O$_5$S: Theoretical: C 48.41; H 7.20; N 12.10; Found: C 47.12; H 7.91; N 12.00.

Chromatography analysis (tlc and hplc) shows no presence of impurities, and the $^1$H n.m.r. spectrum confirms the molecular structure.

Synthesis of tert-butyloxycarbonyl-alanylphenylalanine methyl ester Boc-Ala-Phe-OMe 1.0 equivalent of Boc-Ala is dissolved in anhydrous THF, and 1.1 equivalents of NMM and 1.1 equivalents of isobutyl chloroformate are added to the solution cooled to −15° C. and maintained in a nitrogen atmosphere. After two minutes, 1.0 equivalent of HCl.Phe-OMe and 1.0 equivalent of NMM are added.

During the addition of the isobutyl chloroformate and the HCl.Phe-OMe, the temperature is checked to ensure that it does not exceed −10° C. Having verified the disappearance of HCl.Phe-OMe, the reaction is suspended by evaporating the solvent mixture to dryness. The residue is taken up in EtAc and washed with 5% sodium bicarbonate, water, 5% citric acid and water. The organic solution is dried over magnesium sulphate. The product is obtained by crystallisation from EtAc/petroleum ether.

M.P.=82°–84° C.

$[\alpha]_{22}\cdot^{546} = -22.97$ (C=0.91 in MeOH)

Elementary analysis for C$_{18}$H$_{26}$N$_2$O$_5$: Theoretical: C 61.69; H 7.48; N 8.00; Found: C 61.08; H 7.42; N 7.95.

Chromatography analysis (tlc and hplc) shows no presence of impurities, and the $^1$H n.m.r. spectrum confirms the molecular structure.

Synthesis of tert-butyloxycarbonyl-alanylphenylalanine amide Boc-Ala-Phe-NH$_2$ 1.0 equivalent of Boc-Ala-Phe-NH$_2$ is dissolved in MeOH, and anhydrous ammonia is passed for 30 minutes into this solution cooled to −5° C. The solution, contained in a hermetically sealed vessel, is kept overnight at ambient temperature, after which the solution is evaporated to dryness. The solid residue is washed under hot conditions with Et$_2$O and filtered.

M.P.=167°–168° C.

$[\alpha]_{22}\cdot^{546} = -43.46$ (C=1.37 in MeOH).

Elementary analysis for C$_{17}$H$_{25}$N$_3$O$_4$: Theoretical: C 60.87; H 7.51; N 12.52; Found: C 60.83; H 7.47; N 12.50.

Chromatography analysis (tlc and hplc) and $^1$H n.m.r. show no presence of impurities, and confirm the molecular structure.

Synthesis of tert-butyloxycarbonyl-alanylgemphenylalanine hydrochloride Boc-Ala-gPhe.HCl 1.0 equivalent of Boc-Ala-Phe-NH$_2$ is dissolved in a 2:3 v/v water:MeCN mixture. 1.2 equivalents of TIB dissolved in MeCN are added to the solution at ambient temperature under agitation.

An inert gas is bubbled through the reaction mixture in order to facilitate removal of the CO$_2$ developed during the reaction. Having verified the disappearance of Boc-Ala-Phe-NH$_2$, the reaction is suspended and the reaction solvent is evaporated to dryness. 1.0 equivalent of 0.4N HCl in EtAc is added to the residue after taking up in EtAc. On then adding Et$_2$O, a white precipitate is obtained which is isolated by filtration. The product is obtained by crystallising the precipitate with EtOH/Et$_2$O.

M.P.=135.5°–137° C.

$[\alpha]_{22}\cdot^{546} = -54.15$ (C=1.12 in MeOH).

Elementary analysis for C$_{16}$H$_{26}$N$_3$O$_3$Cl: Theoretical: C 55.88; H 7.62; N 12.22; Found: C 55.81; H 7.58; N 12.07.

Chromatography analysis (tlc and hplc) shows no presence of impurities, and the $^1$H n.m.r. spectrum confirms the molecular structure.

Synthesis of tert-butyloxycarbonyl-alanylgemphenylalanyl-D-benzyloxycarbonyl-phenylalanine Boc-Ala-gPhe-D-Z-Phe 1.0 equivalent of Z-D-Phe are dissolved in DMF, and 1.1 equivalents of HOBt and 1.1 equivalents of DCC dissolved in DMF are added to the solution cooled to 0° C. After 20 minutes, 1.0 equivalent of Boc-Ala-gPhe.HCl and 1.0 equivalent of NMM dissolved in DMF are added to the cold mixture. The ice bath is removed after one hour.

After checking the disappearance of Boc-Ala-gPhe.HCl, the reaction is suspended, the precipitated DCU is filtered off, and the reaction solvent evaporated to dryness. The residue is taken up in CHCl$_3$ and washed with 5% sodium bicarbonate, water, 5% citric acid and water. The organic phase is dried over magnesium sulphate and evaporated to dryness. The required product is obtained by precipitation from THF/petroleum ether.

M.P. = 195°–197° C.

$[\alpha]_{22}{}^{.546} = 8.53°$ (C = 1.48 in DMF).

Elementary analysis for $C_{33}H_{40}N_4O_6$: Theoretical: C 67.32; H 6.85; N 9.51; Found: C 67.02; H 6.79; N 8.45.

Chromatography analysis (tlc and hplc) and $^1H$ n.m.r. show no presence of impurities, and confirm the molecular structure.

Synthesis of tert-butyloxycarbonylalanylgemphenylalanyl-D-phenylalanylmalonylleucylmethionine amide Boc-Ala-gPhe-D-Phe-Gly-Leu-Met-NH$_2$ 1.0 equivalent of HO-mGly-Leu-Met-NH$_2$ is dissolved in THF, and 1.1 equivalents of HOBt dissolved in DMF and 1.1 equivalents of DCC dissolved in THF are added to the solution cooled to 0° C. After 20 minutes, 1.0 equivalent of Boc-Ala-gPhe-D-Phe (obtained by removing the benzyloxycarbonyl group from Boc-Ala-gPhe-D-Z-Phe by catalytic hydrogenation with 10% Pd on carbon) and 1.1 equivalents of NMM dissolved in DMF are added to the cold mixture.

After 20 hours, and having verified the disappearance of Boc-Ala-gPhe-D-Z-Phe, the reaction mixture is filtered. The resultant solution is evaporated to dryness and the solid residue is washed with 5% sodium bicarbonate, water, citric acid, water and methanol.

M.P. = 248°–250° C.

$[\alpha]_{22}{}^{.546} = -25.14$ (C = 1.36 in DMF).

Elementary analysis for $C_{39}M_{57}N_7O_8S$: Theoretical: C 59.74; H 7.33; N 12.51; Found: C 59.58; H 7.09; N 12.45.

Chromatography analysis (tlc and hplc) and $^1H$ n.m.r. show no presence of impurities and confirm the molecular structure.

We claim:

1. Compounds corresponding to general formula I:

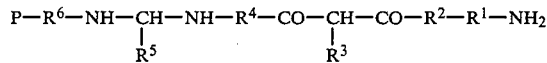

in which P is a hydrogen atom, a linear or branched aliphatic alkyl group with 1–6 carbon atoms, or a saturated or unsaturated linear or branched chain aliphatic acyl group such as formyl, acetyl, propionyl, n-butyryl, isobutyryl, n-valeryl, isovaleryl, hexanoyl, isohexanoyl, heptanoyl, octanoyl, crotonoyl, methacryloyl, acryloyl; or a substituted acyl group such as hydroxyacetyl, 2-hydroxypropionyl, 3-hydroxypropionyl, aminoacetyl, 4-hydroxyphenylacetyl, 4-hydroxyphenylpropionyl, 2-aminopropionyl, 3-aminopropionyl, O-ethyl-malonyl, ethoxyformyl, methoxyacetyl, 3-methoxypropionyl, 3-ethoxypropionyl, chloroacetyl, dichloroacetyl, 2-chloropropionyl, 3-chloropropionyl, 2,3-dichloropropionyl, bromoacetyl, 4-hydroxy-3,5-diiodophenylacetyl, 3-oxobutyryl, 3-oxovaleryl, 4-oxovaleryl, methylthioacetyl, 3-methylthiopropionyl, ethylthioacetyl, 3-ethylthiopropionyl, nicotinoyl, 4-aminobutyryl, $N^\alpha$-[(1-(9-adenyl)$\beta$-D-ribofuranuronosyl)], $N^\alpha$-[(1-(9-hypoxanthyl)-$\beta$-D-ribofuranuronosyl]; or a group such as benzyloxycarbonyl, tert-butyloxycarbonyl, tert-amyloxycarbonyl, isobornyloxycarbonyl, adamantyloxycarbonyl, or chloro or nitro-substituted benzyloxycarbonyl;

$R^1$ is a residue of methionine, methioninesulphoxide, methionine sulphone, selenomethionine, leucine, norleucine, valine or norvaline;

$R^2$ is a residue of leucine, norleucine, valine, norvaline, alanine or isoleucine;

$R^3$ is a hydrogen atom or methyl;

$R^4$ is an amino acid residue of D configuration such as phenylalanine, tryptophan, tyrosine, valine, norvaline, leucine, norleucine, isoleucine, serine or derivatives, threonine or derivatives, histadine or derivatives, methionine, methionine-S-methyl, methionine sulphone, arginine or derivatives, lysine or derivatives, ornithine or derivatives, 2,4-diaminobutyric acid or derivatives, 2,3-diaminopropionic acid or derivatives, glutamic acid or aspartic acid or their suitable derivatives;

$R^5$ is a hydrogen atom or the side-chain of amino acids such as phenylalanine, tyrosine, 4-chlorophenylalanine, O-benzyltyrosine (or their acetyl, cyclopentyl, tert-butyl-oxycarbonyl or 4-hydroxyphenylacetyl derivatives);

$R^6$ is an amino acid residue such as glutamine or derivatives, pyroglutamic acid, alanine, tyrosine, lysine or derivatives, proline, N-formyl-proline, $\beta$-alanine, N-acetyl-$\beta$-alanine, glycine, desaminophenylalanine, desaminoaspartic acid, methyldesaminoaspartic acid, or glutamic acid esters represented by general formula (II):

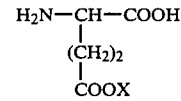

in which X is methyl, ethyl, methoxyethyl, methoxy(ethoxy)$_n$ethyl where n = 1, 2 or 3.

2. The peptide Boc-Ala-gPhe-D-Phe-mGly-Leu-Met-NH$_2$ in which all the amino acids are of L configuration.

3. The peptide cyclopentyl-Ala-gPhe-mGly-Leu-Met-NH$_2$ in which all the amino acids are of L configuration.

4. The peptide Glp-gPhe-D-Phe-mGly-Leu-Met-NH$_2$ in which all the amino acids are of L configuration.

5. The peptide Glp-gPhe-D-Phe-(R,S)mAla-Leu-Met-NH$_2$ in which all the amino acids are of L configuration.

6. The peptide HCO-Pro-gPhe-D-Phe-mGly-Leu-Met-NH$_2$ in which all the amino acids are of L configuration.

7. The peptide HCO-Pro-gPhe-D-Phe-(R,S)mAla-Leu-Met-NH$_2$ in which all the amino acids are of L configuration.

8. The peptide Boc-Pro-gPhe-D-Phe-mGly-Leu-Met-NH$_2$ in which all the amino acids are of L configuration.

9. The peptide Boc-Pro-gPhe-D-Phe-(R,S)mAla-Leu-Met-NH$_2$ in which all the amino acids are of L configuration.

10. The peptide cyclopentyl-Pro-gPhe-D-Phe-mGly-Leu-Met-NH$_2$ in which all the amino acids are of L configuration.

11. The peptide Cyclopentyl-Pro-gPhe-D-Phe-(R,S)mAla-Leu-Met-NH$_2$ in which all the amino acids are of L configuration.

12. The peptide cyclopentyl-Gln-gPhe-D-Phe-mGly-Leu-Met-NH₂ in which all the amino acids are of L configuration.

13. The peptide cyclopentyl-Gln-gPhe-D-Phe-(R,S)mAla-Leu-Met-NH₂ in which all the amino acids are of L configuration.

14. The peptide Pyr-gPhe-D-Phe-mGly-Leu-Met-(O)-NH₂ in which all the amino acids are of L configuration.

15. The peptide Pyr-gPhe-D-Phe-(R,S)mAla-Leu-Met(O)-NH₂ in which all the amino acids are of L configuration.

* * * * *